United States Patent [19]
Matsui et al.

[11] Patent Number: 5,535,750
[45] Date of Patent: Jul. 16, 1996

[54] METHOD AND APPARATUS FOR EVALUATING THE PROGRESS OF OSTEOPOROSIS BY ULTRASONIC SIGNALS

[75] Inventors: Kazuyuki Matsui, Neagari-machi; Akio Nakahashi, Matto; Kohji Higashi, Kanazawa; Fumio Nogata, Himeji, all of Japan

[73] Assignee: Kabushiki Kaisha Ishikawa Seisakusho, Ltd., Kanazawa, Japan

[21] Appl. No.: 312,974

[22] Filed: Sep. 30, 1994

[51] Int. Cl.$^6$ ..................................................... A61B 8/08
[52] U.S. Cl. ........................................................ 128/661.03
[58] Field of Search ......................... 128/660.01, 660.02, 128/660.06, 660.07, 660.08, 661.03; 73/599, 602; 364/413.25

[56] References Cited

U.S. PATENT DOCUMENTS

| | | | |
|---|---|---|---|
| 3,847,141 | 11/1974 | Hoop | 128/2 V |
| 4,913,157 | 4/1990 | Pratt, Jr. et al. | 128/661.03 |
| 4,926,870 | 5/1990 | Brandenburger | 128/660.01 |
| 4,930,511 | 6/1990 | Rossman et al. | 128/661.03 |
| 4,941,474 | 7/1990 | Pratt, Jr. | 128/660.01 |
| 4,976,267 | 12/1990 | Jeffcott et al. | 128/660.01 |
| 5,029,475 | 7/1991 | Kikuchi et al. | 128/661.03 X |
| 5,134,999 | 8/1992 | Osipov | 128/661.03 |
| 5,197,475 | 3/1993 | Antich et al. | 128/660.01 |

FOREIGN PATENT DOCUMENTS

| | | |
|---|---|---|
| 1-503199 | 11/1989 | Japan . |
| 2-104337 | 4/1990 | Japan . |
| 4-501519 | 3/1992 | Japan . |

*Primary Examiner*—Francis Jaworski
*Attorney, Agent, or Firm*—Burns, Doane, Swecker & Mathis

[57] ABSTRACT

An ultrasonic signal is transmitted to a heel bone or patella of a person being examined to obtain data of velocity of transmission propagation. The data which is obtained is computerized through calculation to compute a two-dimensional ratio of a compact bone to a bone structure (Au) from a one-dimensional ratio of a compact bone to a bone structure (Eu). Then, a chart is drawn to suffice an Au for which a fractal geometry is utilized to compare the chart with an image of an Au of a healthy person who is under the same condition in sex and age. The portions different from each other are then sorted by color for evaluating the progress of osteoporosis.

13 Claims, 10 Drawing Sheets

METHOD AND APPARATUS FOR EVALUATING THE PROGRESS OF OSTEOPOROSIS BY ULTRASONIC SIGNALS

BACKGROUND OF THE INVENTION

1. Technical Field of the Invention

The present invention relates to a method and apparatus for evaluating the progress of osteoporosis by utilizing ultrasonic signals.

2. Description of Related Art

With an increase in population of aged people, there is a rapid increase in number of patients who suffer from a disease called osteoporosis, which causes fractures of bones, and it is becoming a great concern in the medical field. With a decrease in the calcium content in a bone structure, cracking and damage of bones are easily caused by deterioration in the strength of bone. About 30% of women and about 10% of men who are more than 60 years old are said to be suffering from osteoporosis. If a symptom of osteoporosis is discovered at an early stage, it may be possible to effectively prevent the progress of the disease with a variety of medical treatments. It is, therefore, very important to undergo a medical examination at regular intervals in order to detect the disease in its early stages. Heretofore, it has been practiced to preestimate the degree of progress of the osteoporosis by measuring bone mineral content (BMC) by roentgen irradiation (D-ray) or by gamma radiation.

However, the radiation is very harmful to the living body, and people ranging from about 50 to over 60 years old who might have osteoporosis and post-menopausal women have had to undergo such a hazardous medical examination by the use of radiation. In order to avoid such a hazardous treatment, there have been proposed apparatuses for evaluating osteoporosis by utilizing ultrasonic signals which are not harmful to the human body.

For example, there have been proposed some apparatuses wherein an ultrasonic signal is transmitted to a patient to determine a velocity of sound and attenuation in a bone structure from a signal received, and the data received are used as indicators for evaluation of the disease (for example JP-A-1-503199, JP-A-2-104337, and JP-A-4-501519).

As shown in FIG. 17 of the accompanying drawings, an indicator of 'stiffness' which is computerized from information obtained by transmission of an ultrasonic signal is plotted on the vertical axis, and 'age' is plotted along the horizontal axis to draw a graph of the data of an average healthy person. Then, an indication is made, by plotting the data thereon, to show how different a patient (person being examined) is from a healthy person, and a determination is made whether the patient is under normal condition or the patient requires immediate medical treatment.

From the standpoint of a patient, the patient may understand how far his condition is from an image displayed comparing with a standard curved line of a healthy person. However, the patient hardly obtains a satisfactory explanation how it relates to the progress of osteoporosis and how the condition of the disease is progressing even if he asks for an explanation from doctors and nurses.

SUMMARY OF THE INVENTION

An object of the present invention is to provide a method and apparatus for evaluating the progress of osteoporosis wherein a computerized image is provided to show the internal condition of a bone structure so that doctors and nurses may easily explain the progress of the disease to the patient (person being tested) while the patient may recognize the progress of the disease from the image displayed on the computer.

In recent years, it has become a serious problem that there are many people who suffer from infection in hospital by Methicillin Resistance *Staphylococcus Aureus* (MRSA). MRSA, which may cause an infection in hospital, is not strong enough to cause harm to a healthy person, however, aged people and those of declining physical strength are affected by the infection, and easily attacked with the disease. Generally, osteoporosis is related to aged people, and therefore such a problem of infection in hospital cannot be ignored.

In the use of a conventional ultrasonic transducer which is provided with a container bag on its head portion, it has been practiced to serilize by alcohol the surface of the container bag and the measured part of the patient, however, there still remains a risk of infection in hospital by the MRSA.

Another object of the present invention is to provide an apparatus for diagnosing osteoporosis wherein a container bag which always comes in contact directly with a patient (person being tested) is abandoned after an examination is finished, and is replaced with a new container bag for every patient so that possible risk of infection can be avoided.

The feature of the present invention is to display a simulated image of a bone which represents the bone condition of a patient based on a quantitative parameter showing a feature of the shape of a bone by making use of characteristics of a large difference in the velocity which is made when an ultrasonic signal is propagated through a bone (solid matter) and marrow (liquid) in a hard tissue wherein a ratio in length between the solid matter and liquid is found while obtaining a ratio of area a bone occupies by measuring it in two directions intersecting at right angles or by measuring it at more than two portions in the same plane (like a movement of an iron when ironing).

More particularly, when osteoporosis is evaluated by utilizing ultrasonic signals, an ultrasonic signal is transmitted into a heel bone or patella of a person being examined to determine a velocity of transmission propagated in a bone structure. Then, based on the propagation velocity of transmission obtained, a two-dimensional ratio of a compact bone to a bone structure (hereinafter called Au) is computed from a one-dimensional ratio of a compact bone to a bone structure (hereinafter called Eu) by a predetermined calculation formula. By making use of a fractal dimension which corresponds with said Eu, a chart which suffice said Au is then drawn by utilizing a computerized drawing program preliminarily provided. By comparing the image drawn on the chart with an image of a bone of a healthy person, the progress of osteoporosis is evaluated.

A container bag which contains mixed solution is removably attached to the head of an ultrasonic probe. More particularly, an expandable container bag which contains liquid such as water and mixed solution is fixed to a cassette in a manner to position its protrusion in a lateral direction.

The other side of the cassette which is the opposite side of the protrusion is removably attached to the outer circumference of said ultrasonic probe so as to closely contact with the head of the probe.

When the progress of osteoporosis is evaluated, for example, a pair of ultrasonic probes consisting of transmitter and receiver are brought into contact with a heel bone, and a propagation time transmitted through a bone structure is measured. A velocity of propagation is worked out from the measured propagation time, from which an approximate aerial ratio of compact bone at the heel portion is obtained using a predetermined formula, and by utilizing fractal geometry, an imitative bone image which represents an actual bone condition is drawn and displayed on the computer screen. Comparing with a shape of bone of a healthy person, the image displayed is sorted by color showing a portion of lost bone in red.

On the other hand, when an effect of medical treatment gradually appears after diagnosis as osteoporosis, a portion of increased bone is colored in blue to show a change by color. By recognizing an area sorted by color, a patient (person being examined) is able to practically grasp the progress of the disease, or, on the contrary, the effect of the medical treatment being undertaken.

At the time of measurement, a container bag of said ultrasonic probe which is brought into contact with the heel of a patient (person being examined) is replaced with a new one for every patient together with a cassette to which the container bag is fixed so that any possibility of receiving infection in hospital can be avoided.

These and other objects and features of the present invention will become more apparent from the following description taken in conjunction with the accompanying drawings which illustrate specific embodiments of the invention.

DESCRIPTION OF THE PREFERRED EMBODIMENT

Referring to the accompanying drawings, there will now be described an apparatus to which the present invention is applied.

Figure 1:
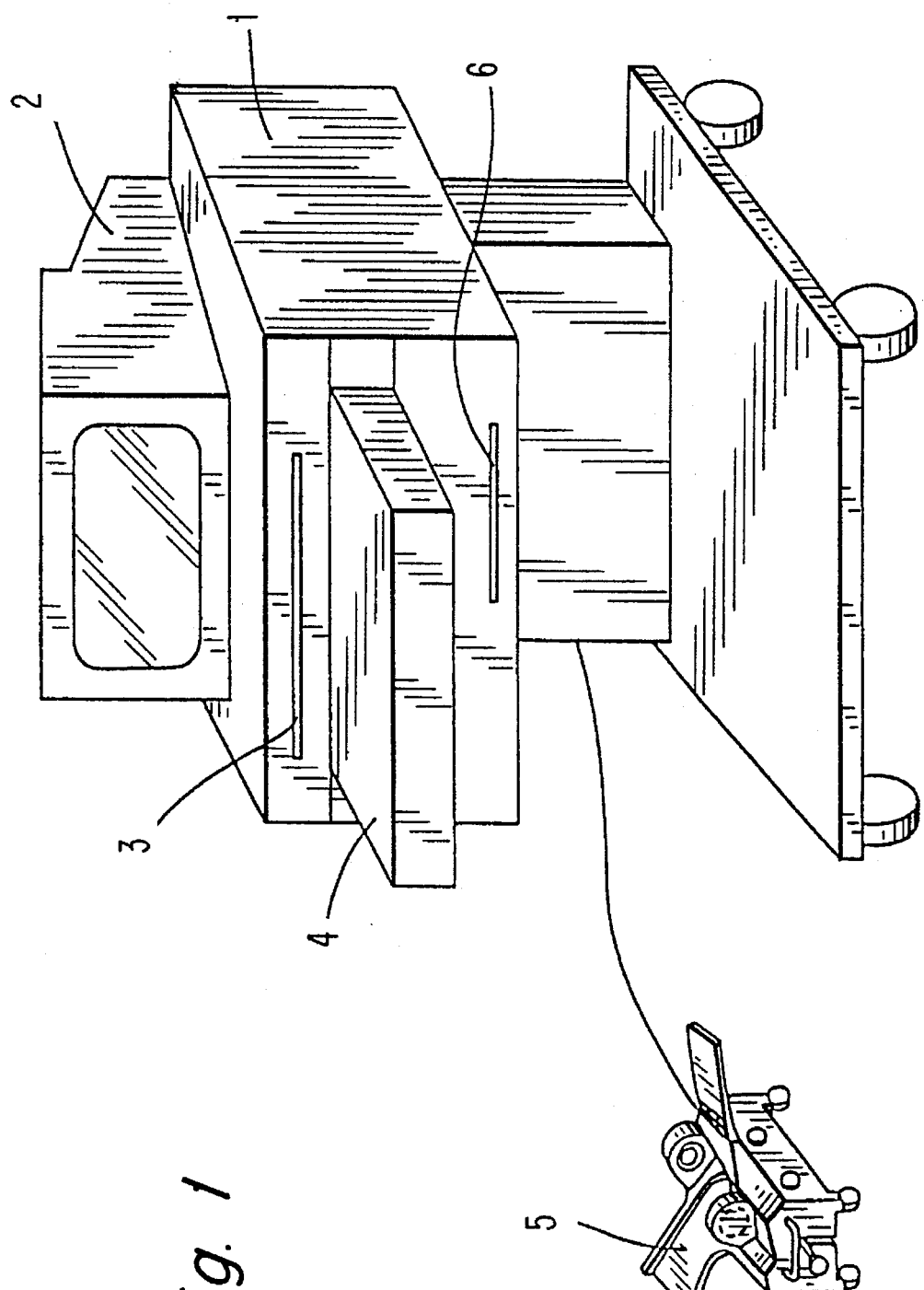
FIG. 1 is a perspective view showing schematically an apparatus for evaluating osteoporosis to which the present invention is applied.

In FIG. 1, numeral 1 represents a main body of a computer including CPU, ROM, RAM, 2 represents a CRT for display, 3 a printer, 4 a keyboard for input processing, 5 a measuring section provided with a footboard for placing a foot of person being examined, and ultrasonic probes connected to an ultrasonic transmitting transducer and an ultrasonic receiving transducer, and 6 a floppy disk of auxiliary storage.

Figure 2:
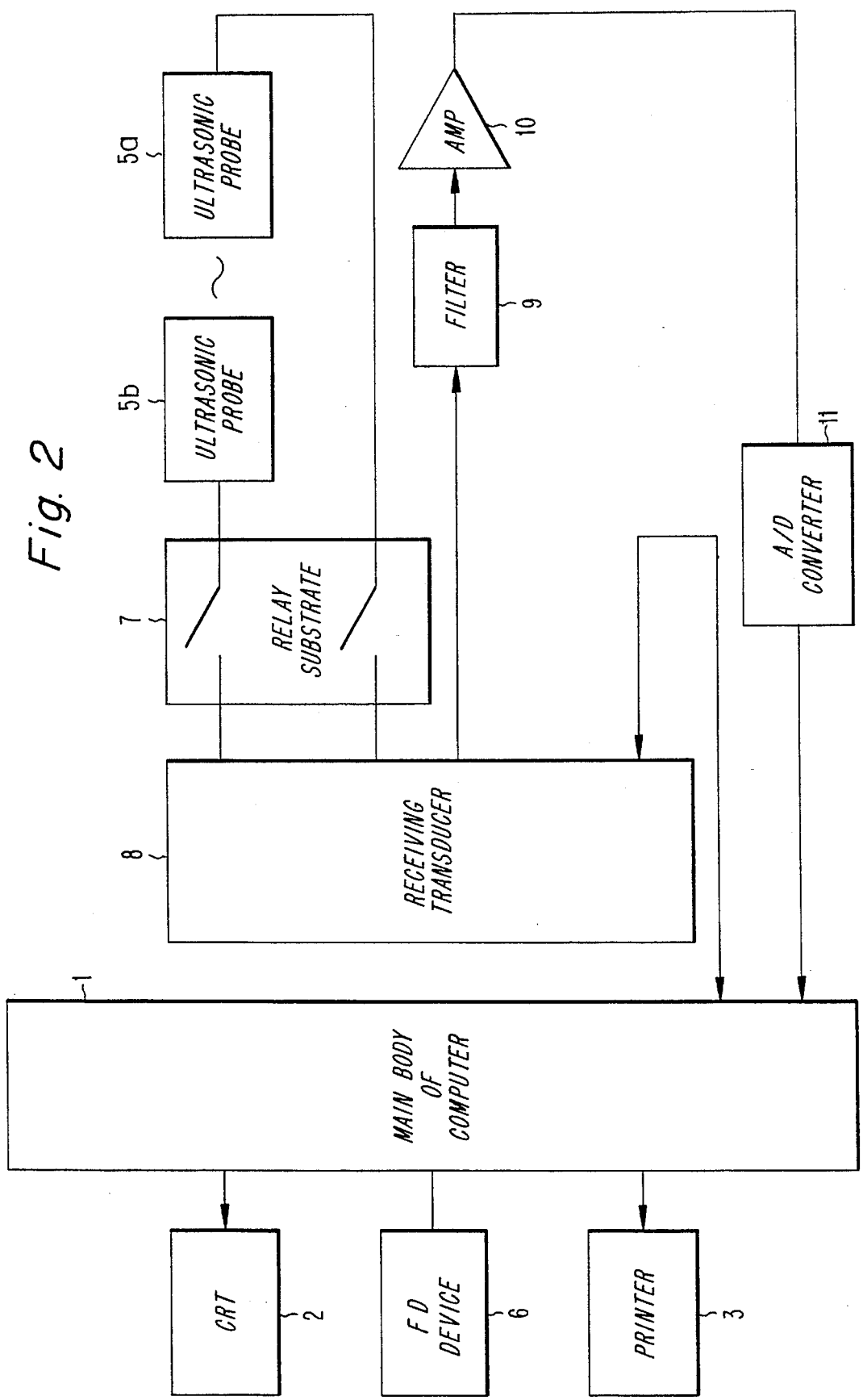
FIG. 2 is an explanatory view showing an electric circuit of the apparatus shown in FIG. 1.

FIG. 2 is an electric circuit diagram showing a relation how the measuring section 5 which includes ultrasonic probes connected to ultrasonic transmitting and receiving transducers is connected with the computer, wherein each one of the ultrasonic probes 5a and 5b are connected with ultrasonic transmitting and receiving transducers 8 through a relay substrate 7. An electric pulse signal transmitted from the ultrasonic probe 5a is converted to an ultrasonic signal by a piezoelectric element to be transmitted toward the ultrasonic probe 5b. In the ultrasonic probe 5b, the ultrasonic signal is converted to an electric signal again by a piezoelectric element.

The ultrasonic transmitting and receiving transducers 8 are connected with an A/D converter 11 through a filter 9 and amplifier 10. The filter 9 eliminates low and high frequency from RF signal of the ultrasonic transmitting and receiving transducers 8, and transmits a signal to the amplifier 10.

The A/D converter, on the other hand, converts a signal transmitted from the amplifier 10 into a digital signal to send data to the CPU in the main body of the computer 1.

Based on a signal transmitted from the ultrasonic transmitting and receiving transducers 8, the CPU in the main body of the computer 1 performs a computing process to assume a two-dimensional ratio of a compact bone to a bone structure (hereinafter called Au) and a shape of the bone structure. The ultrasonic transmitting and receiving transducers 8 are also connected with the CPU in the main body of the computer 1. On the other hand, the CPU is connected with the CRT 2, printer 3 and FD device 6 to output the result of a computation to those devices. The CPU also stores memory.

Figure 3:
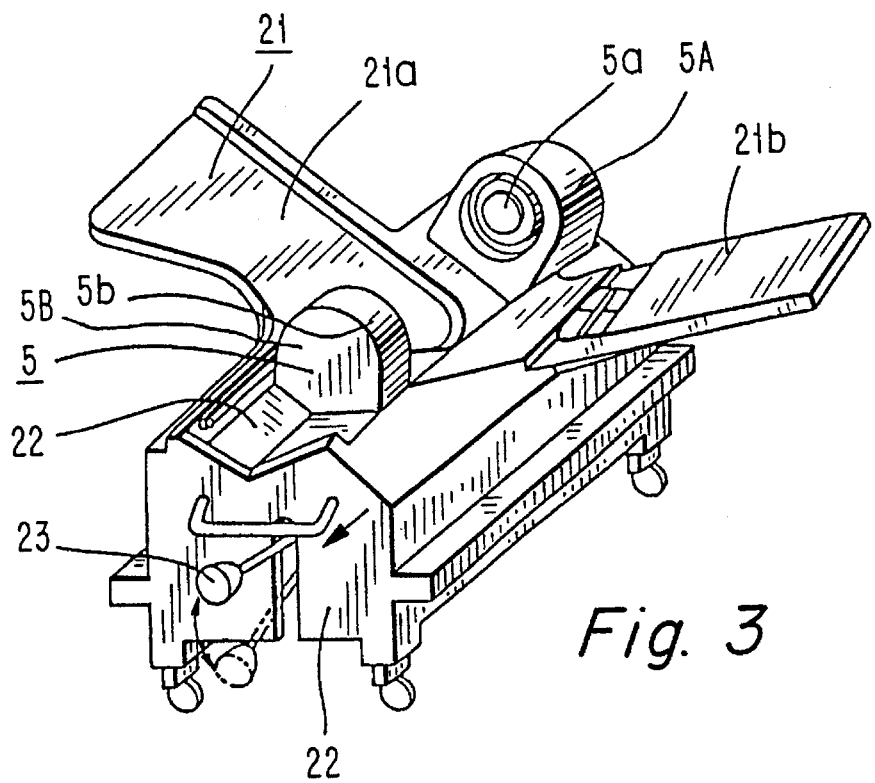
FIG. 3 is a perspective view schematically showing a measuring section provided with ultrasonic probes.

FIG. 3 shows the appearance of an essential part of said measuring section 5 which is provided with ultrasonic probes connected with the ultrasonic transmitting and receiving transducers. A footboard 21 is bent substantially at a right angle, and consists of a surface 21a which supports the sole of a foot and a surface 21b which supports a leg portion. The footboard 21 is fixed on a base 22.

The ultrasonic probe 5a is fixed on the side of the base 22, and the other ultrasonic probe 5b is loosely fitted to a groove 22a which is provided in the base 22. Further, the probe 5b is attached movably in a lateral direction by operation with a handle 23.

Figure 6:
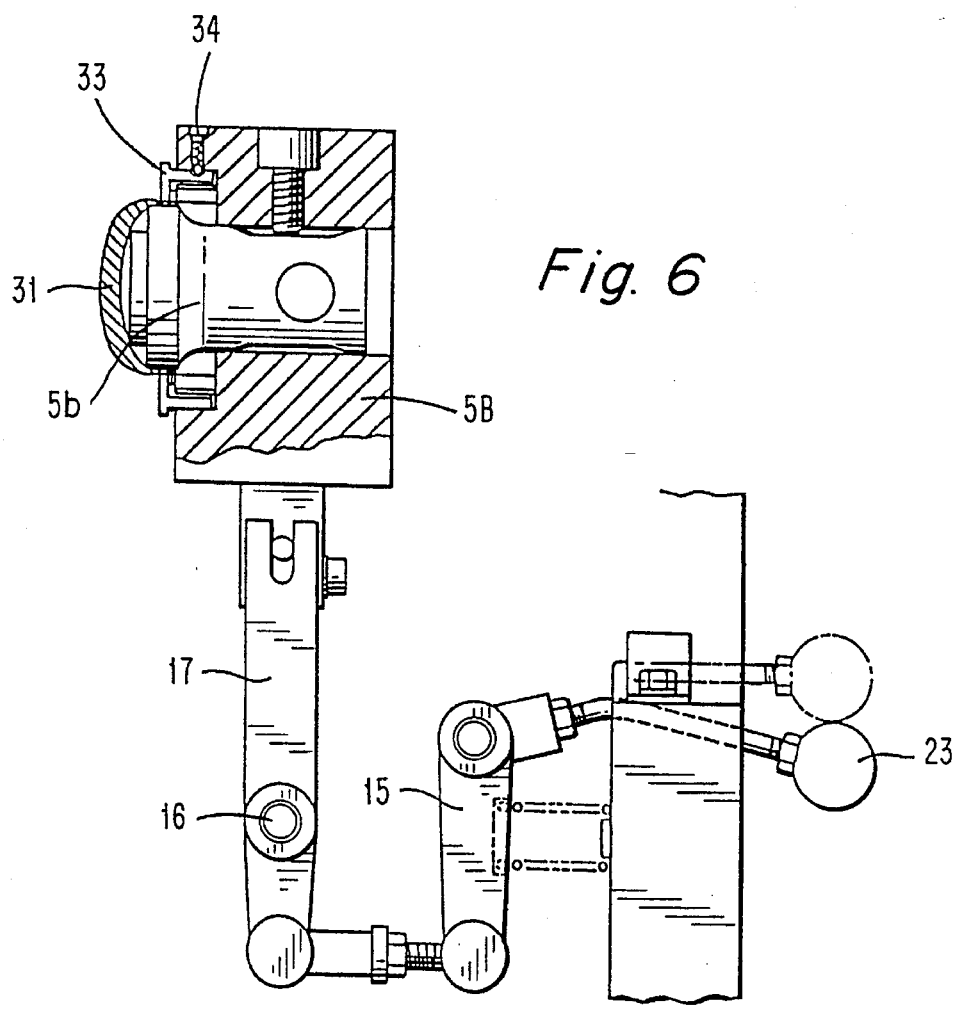
FIG. 6 is an explanatory view showing an example of a moving device by which ultrasonic probes attached to a cassette are moved.

More particularly, when the handle 23 is moved vertically as shown in FIG. 6, a lever 17 is moved laterally with a shaft 16 as fulcrum by a link-lever mechanism, and a slide block 5B to which the ultrasonic probe 5b is fixed is moved laterally in a horizontal direction.

Figure 4:
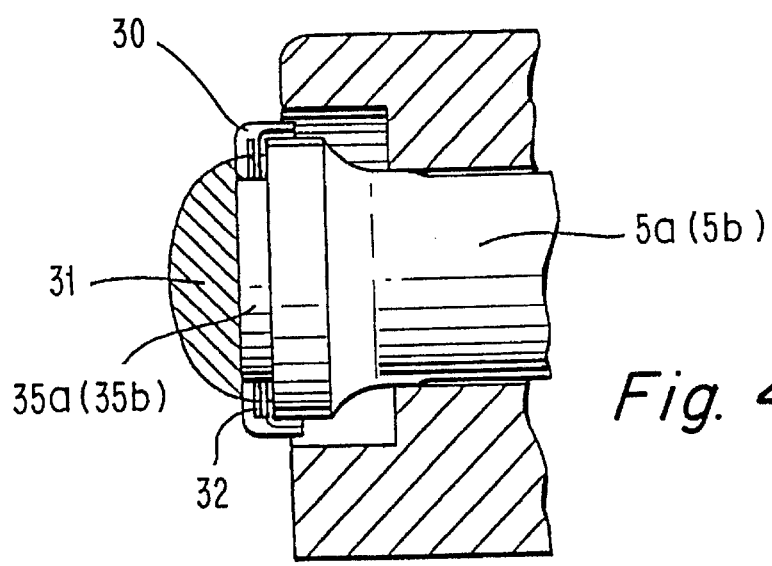
FIG. 4 is a sectional view showing a relation between ultrasonic probes and a container bag.

A film container bag 31 made of synthetic resin is filled with water end gelled liquid, and is fixed to a thin cylindrical cassette 30 through a round washer 32 in the inside of a hollow section such that it is protruded spherically in a lateral direction as illustrated in FIG. 4. The cassette 30 is screwed on the outer circumference of the ultrasonic probes 5a and 5b so as to closely contact with the bag 31 having the spherical protrusion and head portions 35a, 35b of the ultrasonic probes 5a, 5b on the other side.

Figure 5:
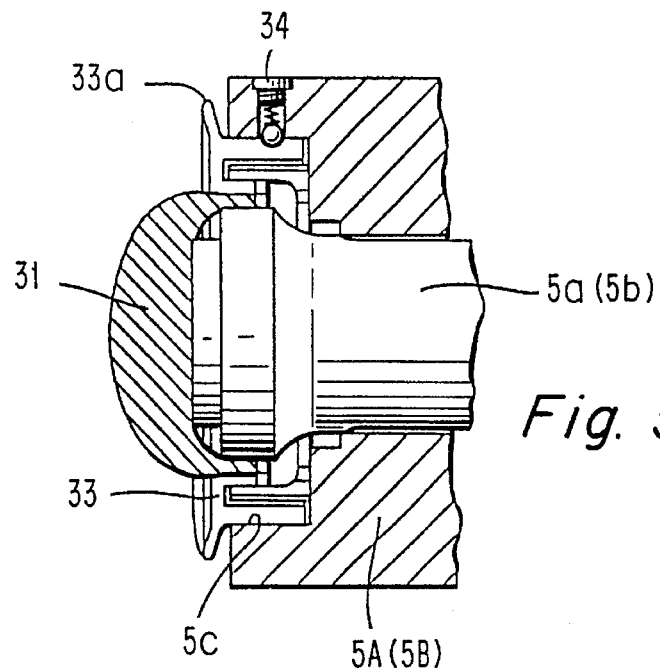
FIG. 5 is a sectional view showing another sample of a cassette to which the container bag shown in FIG. 4 is fixed.

As shown in FIG. 5, a cassette 33 which is fixed to the spherical container bag 31 is removably attached to the internal circumference in the hollow sections of the blocks 5A and 5B. More particularly, since the outer circumference of the cassette 33 is fixed by a ball and spring mechanism 34, the cassette 33 to which the container bag is fixed may be removed by a one-touch operation by pushing or pulling a flange section 33a of the cassette 33. In place of the container bag 31, a container made of silicone may also be preferably utilized.

Figure 7:
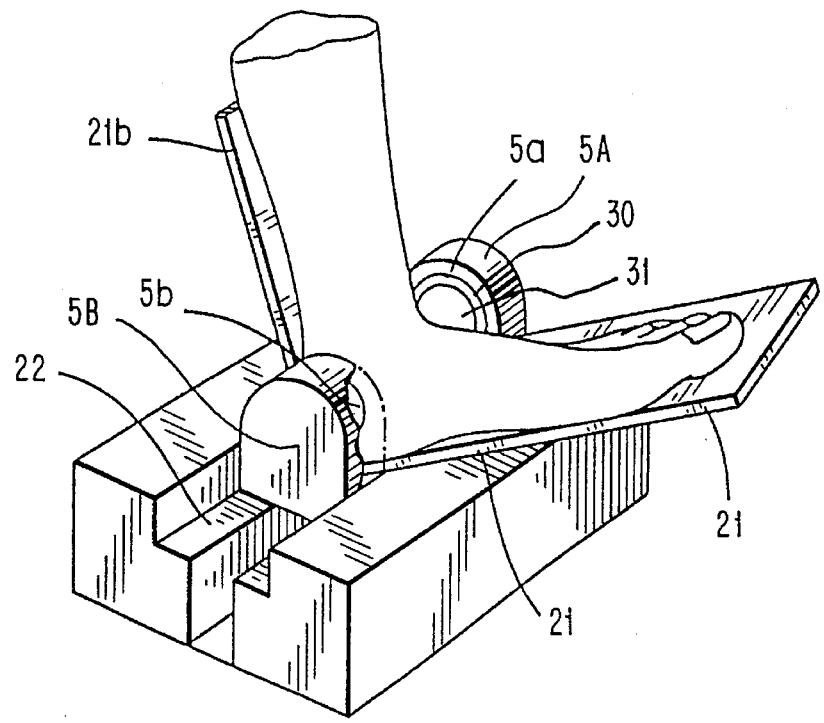
FIG. 7 is an explanatory view showing how a measurement is conducted by transmitting an ultrasonic signal to a heel bone.

When a foot of patient (person being examined) is placed on the footboard 21 as illustrated in FIG. 7, in other words at the time an ultrasonic signal is transmitted for making a measurement and diagnosis of osteoporosis, the heel comes into contact with the side of the ultrasonic probe 5a. Then, another ultrasonic probe 5b is moved laterally by operating the handle 23 to be brought into contact with the other side of the heel in order to hold the heel between the ultrasonic probes 5a and 5b. A measurement and diagnosis of osteoporosis is conducted under such a state by transmitting ultrasonic signals. When the measurement and diagnosis are finished, the ultrasonic probe 5b is moved away from the heel by operating the handle 23.

Prior to placing a foot of new patient (person to be examined) on the footboard 21, either one of the cassette 33 or cassette 30 which is provided with the container bag 31 is removed from the block 5A or slide block 5B to be replaced with a cassette 33 or 30 to which a new container bag 31 is fixed.

In the case of the cassette 30 shown in FIG. 4, for example, the ultrasonic probes 5a, 5b are unscrewed for replacement. On the other hand, in the case of the cassette 33 illustrated in. FIG. 5, the cassette is pulled out of the hollow section of the block 5A or slide block 5B by pulling the flange section 33a. Since the outer circumference of the cassette 33 is attached by the ball and spring mechanism 34, it may be easily replaced by a one-touch operation.

An ultrasonic signal is transmitted from the ultrasonic probe 5a and is received by the other ultrasonic probe 5b. As shown in FIG. 2, a signal from the ultrasonic probe 5b is transmitted to the ultrasonic transmitting and receiving transducers 8 through the relay substrate 7, and the time an ultrasonic signal transmits through a bone structure is measured. Then, a signal from the ultrasonic transmitting and receiving transducers 8 is transmitted to the main body of the computer 1 through the filter 9, amplifier 10 and A/D converter 11. In the main body of the computer 1, a velocity of propagation of the ultrasonic signal transmitting through the bone structure is computed from the measured ultrasonic transmitting time since the distance between the ultrasonic probes 5 and 5b is known.

A one-dimensional ratio of a compact bone to a bone structure (hereinafter called Eu) is computed from the measured velocity of propagation by the following equation 1.

$$Eu = \frac{1/Va - 1/Vb}{1/Va - 1/Vc} \qquad \text{Equation 1}$$

where,

Vb: Ultrasonic propagation velocity in bone

Va: Ultrasonic propagation velocity in marrow (1500 m/s)

Vc: Ultrasonic propagation velocity in compact bone (3000 m/s)

The Eu is an approximate percentage of compact bone (solid substance) against marrow (liquid) and compact bone (solid substance) seen in one dimension (longitudinal direction). In other words, the ultrasonic propagation velocity in bone measured as described above is an average velocity transmitted through the entire portion, since the heel and knee generally consist of soft tissue (skin and flesh portions) and hard tissue (bone portion), and the hard tissue (bone portion) consists of cortical bone, cancellous bone (mixture of bone and marrow) and marrow. Accordingly, the heel bone is considered to be the most proper portion for an examination, as it is known to be occupied by cancellous bone for nearly 95%, and osteoporosis tends to appear in a cancellous bone at first stage, so as to obtain the nearest possible one-dimensional ratio of a compact bone.

An Au is obtained from the Eu which has been obtained, by the following equation 2.

$$Au = Eu \times Eu \qquad (2)$$

The Au is an approximate percentage of a compact bone (solid substance) against the compact bone (solid substance) and marrow (liquid) in a fixed area. The data which have been measured by ultrasonic signals are calculated by the computer and expressed on a two-dimensional image as an imitative view of an inner bone structure.

Figure 8:
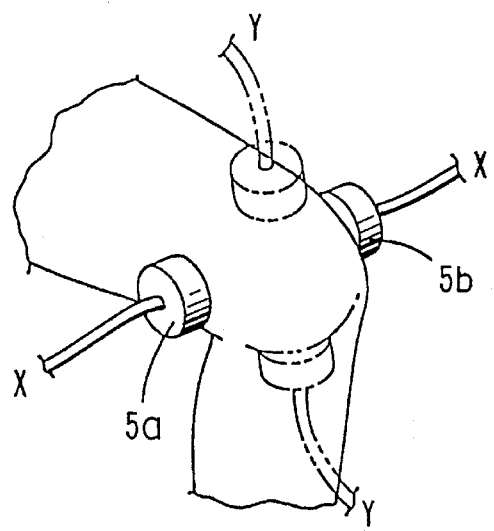
FIG. 8 is an explanatory view showing how a measurement is conducted by transmitting an ultrasonic signal to a patella.

FIG. 8 shows a case when a knee portion is measured by ultrasonic signals in place of a heel portion shown in FIG. 7. In this case, a pair of the ultrasonic probes 5a and 5b are brought in contact with the knee in a horizontal direction (X—X direction) and a vertical direction (Y—Y direction) which intersects the X—X direction at a right angle for measurement. From an ultrasonic propagation velocity which has been obtained, an Eu is determined by the equation 1 for both X direction and Y direction. Then, an Au is computed from the Eu, by the following equation 3.

$$Au = Eux \times Euy \qquad (3)$$

A diagram which suffice said Au is then drawn by utilizing a predetermined drawing program, and a fractal dimension is obtained from an image drawn.

A method of artificially drawing a diagram of the shape of a bone will be described hereinafter seeing a geometrical pattern of a bone in bone structure as two-dimensional.

Figure 9:
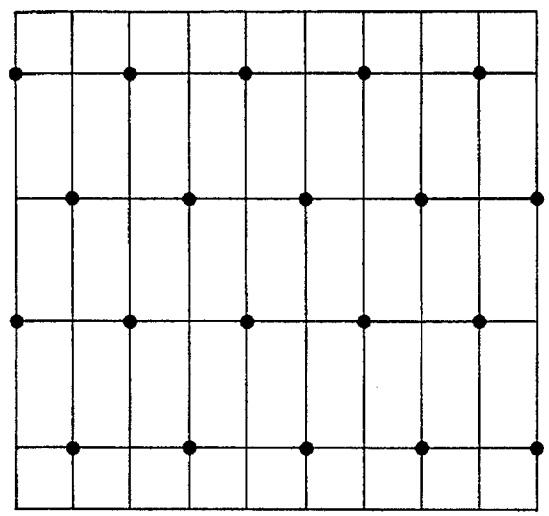
FIG. 9 is an explanatory view showing a case when a shape of cancellous bone is drawn with assistance of computer.

First, a square (picture element of 240×240, for example) is drawn as a foundation, and then elliptical basic holes (P×Q pieces) are punched. The central coordinates of basic holes are made as points on a zigzag lattice as shown in FIG. 9 in order to eliminate excessive irregularities in the thickness of a bone on an image of the bone. Then, n pieces of osteoclast developed into m stages are generated on the surface of the bone to approximate it to the shape of the geometrical pattern of a bone.

Figure 10:
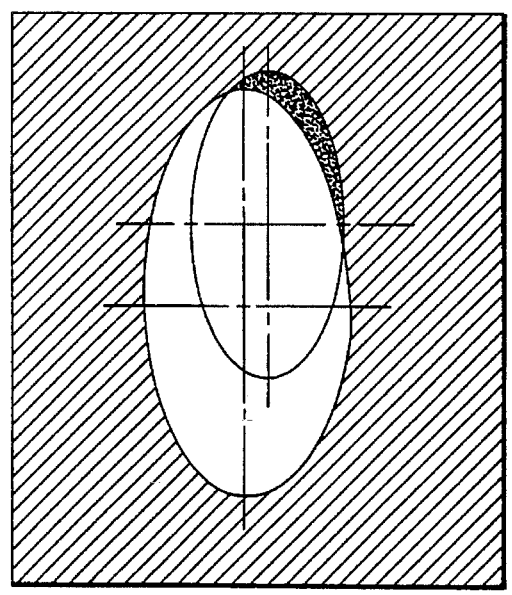
FIG. 10 is another explanatory view showing a case when a shape of cancellous bone is drawn with assistance of computer.

More particularly, an elliptical hole which is smaller than the basic hole is punched centering at a position deflected to some degree from the central coordinates of the basic hole, and the portion painted in black is considered as a portion where the bone is destroyed as illustrated in FIG. 10. In FIG. 10, the portion indicated by oblique lines represents a structure of bone. At this stage, a fractal dimension is affected by the size and number of basic holes, or by the values of m and n.

Figure 11:
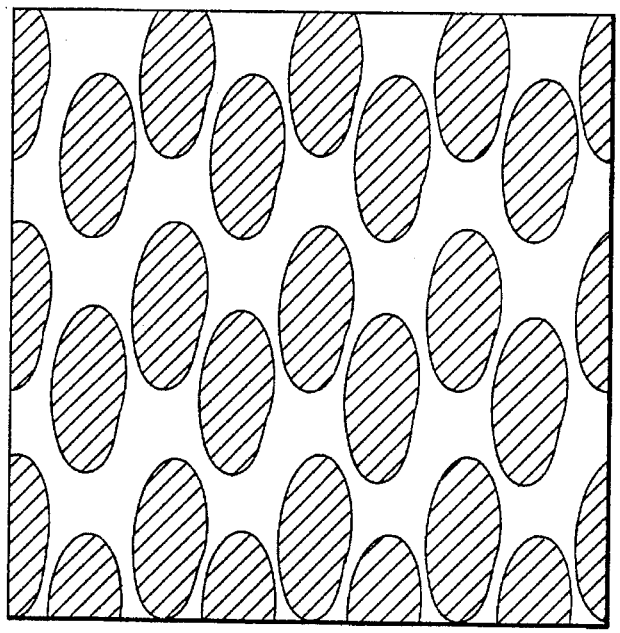
FIG. 11 is an explanatory view showing a shape of cancellous bone drawn by a computer simulation.

A shape of a bone which is artificially drawn is illustrated in FIG. 11. In this figure, the portion indicated by oblique lines represents marrow, and the white portion represents a structure of bone.

Figure 12A:
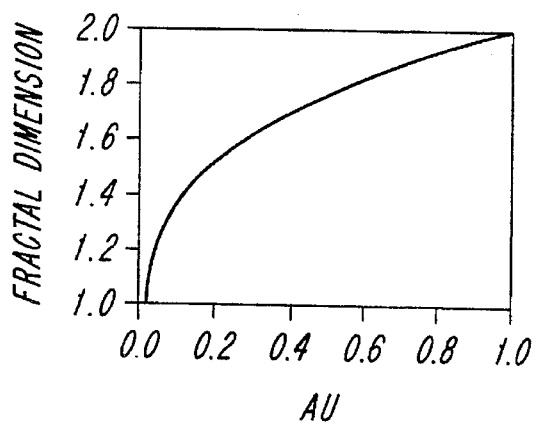
FIGS. 12A and 12B are graphs showing a relation between an Au and a fractal dimension.

A relation between an Au which has been found by the artificial drawing and a fractal dimension is shown in FIG. 12A.

Figure 12B:
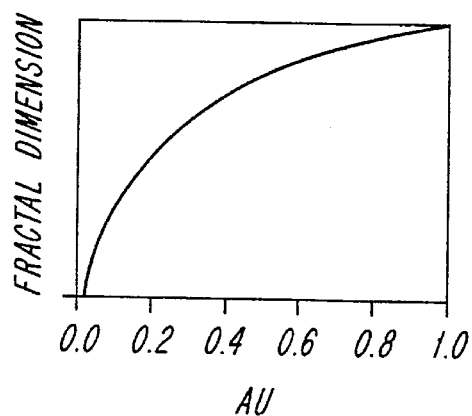

At a first stage, an Au and a fractal dimension are preliminarily obtained. More specifically, seeing a geometrical pattern of the bone two-dimensionally, the Au is adjusted into a fractal dimension. Then, the fractal dimension is represented on the vertical axis and the Au on the transverse axis. As shown in FIG. 12B, the entire bone is laid over one another on one line on a curved line. The Au S and the fractal dimension D are thus expressed by the following approximate equation 4.

$$D = 1 + S^{0.4} \tag{4}$$

The fractal dimension and the Au which has been obtained from said formula, and an Au and a fractal dimension of the subject are then compared. When both the Au and fractal dimension agree, the image drawn by utilizing the drawing program of the computer (refer to FIG. 11) is recognized as an image of bone of the person being examined.

In other words, when the shape of an actual bone and the shape of the bone which has been drawn are compared, two of the shapes appear to look very alike if the Au and fractal dimension are substantially the same. Therefore, the shape of the bone drawn by the computer is considered as one of the shapes of a bone representing an Au. Conversely, a fractal dimension is obtained by finding an Au by an ultrasonic measurement, and a diagram showing the shape of a bone in the Au can be obtained.

Figure 13:
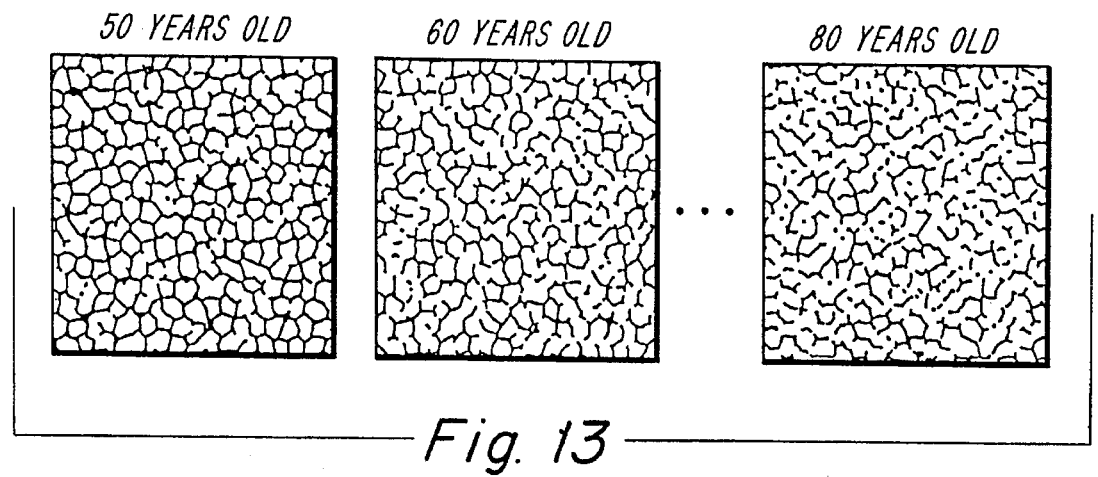
FIG. 13 is an explanatory view showing shapes of cancellous bone of healthy persons drawn by a computer simulation by age group.
Figure 14:
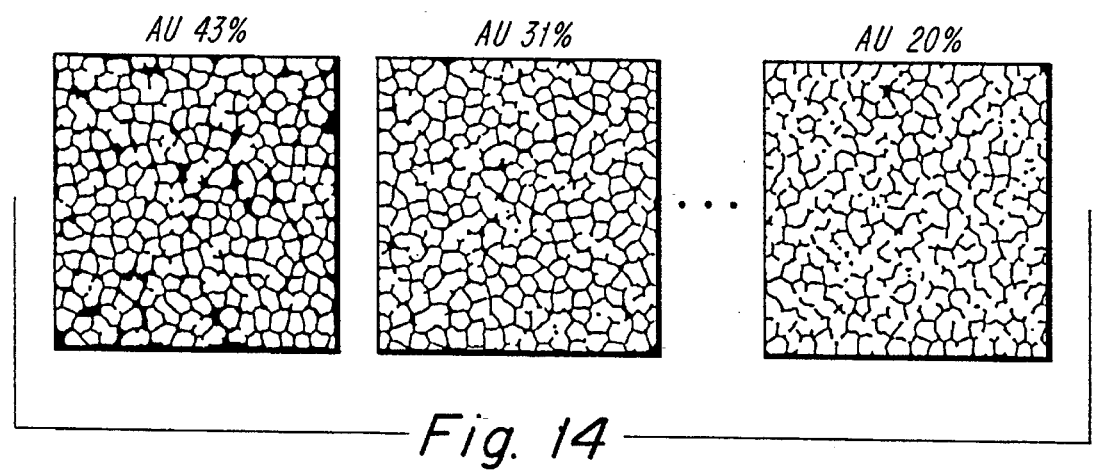
FIG. 14 is an explanatory view showing shapes of cancellous bone based on the Au drawn by a computer simulation in stages.

Comparing an image of a bone of a healthy person of approximately the same sex and age with the image which has been recognized as described above, the progress of osteoporosis can be evaluated. More particularly, a wide range of bone images, each image corresponding to each Au, which represent various bone conditions in stages shown as in FIG. 14 are preliminarily drawn by the computer 1 and stored in the ROM. Apart from the data according to the Au as described above, a range of images showing the condition of a bone of a healthy person by age group as in FIG. 13 can be also preliminarily prepared and stored in the ROM. These images are drawn imitatively by utilizing the good correlation between the Au and the fractal dimension and the self-similarity of the cancellous bone structure, which are most similar to an actual bone image, so that a patient can visually perceive his/her condition of a bone.

Sample of Evaluation 1

In a measurement conducted for a woman aged 65, an ultrasonic propagation velocity was 1680 m/s. An Au at this time was found to be 21.5% through a calculating process made by the computer 1 based on the equations 1 and 2, and a fractal dimension was 1.54 by the equation 4.

On the other hand, an ultrasonic propagation velocity and an Au of a healthy woman aged 65 were counted as 1790 m/s and 27%, and a fractal dimension as 1.59 respectively.

Figure 15A:
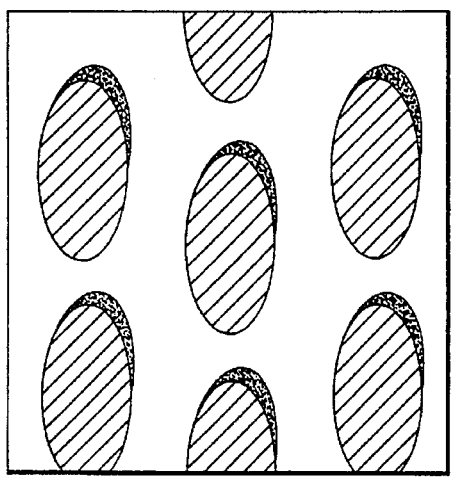
FIGS. 15A and 15B are explanatory views showing shapes of cancellous bone drawn by a computer simulation based on the Au of a person being examined and that of a healthy person.
Figure 15B:
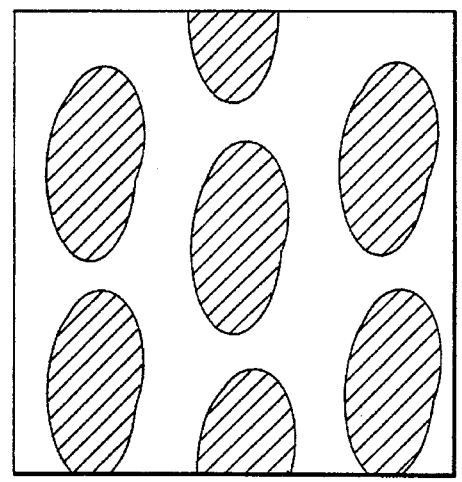

A computerized image of a bone in the heel bone of the person examined is shown in FIG. 15A, and a computerized image of a bone of the healthy person is shown in FIG. 15B. Both the images of the subject and healthy person are indicated on the same display. At the same time, the image of the subject is sorted by color for the portion a bone structure is reduced (the portion painted in black in the figure) compared with the image of the healthy person. Then, an evaluation is made that an osteoporosis of the subject is being progressed (white portion represents a structure of bone, and the portion illustrated by oblique lines represents marrow in FIGS. 15A and 15B).

Sample of Evaluation 2

Figure 16A:
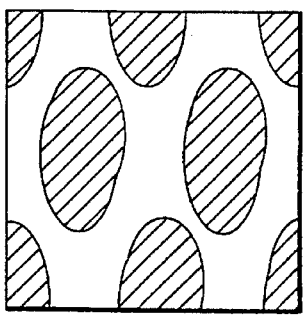
FIGS. 16A–C are explanatory views showing shapes of cancellous bone drawn by a compute simulation based on the Au of the same person in stages with passage of time.
Figure 16B:
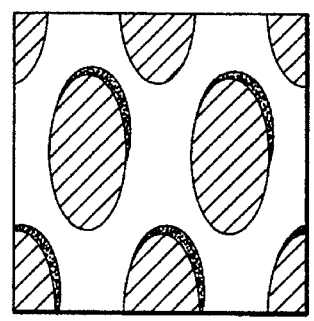
Figure 16C:
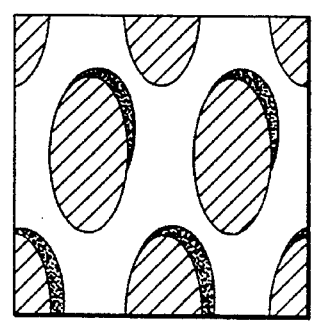
Figure 17:
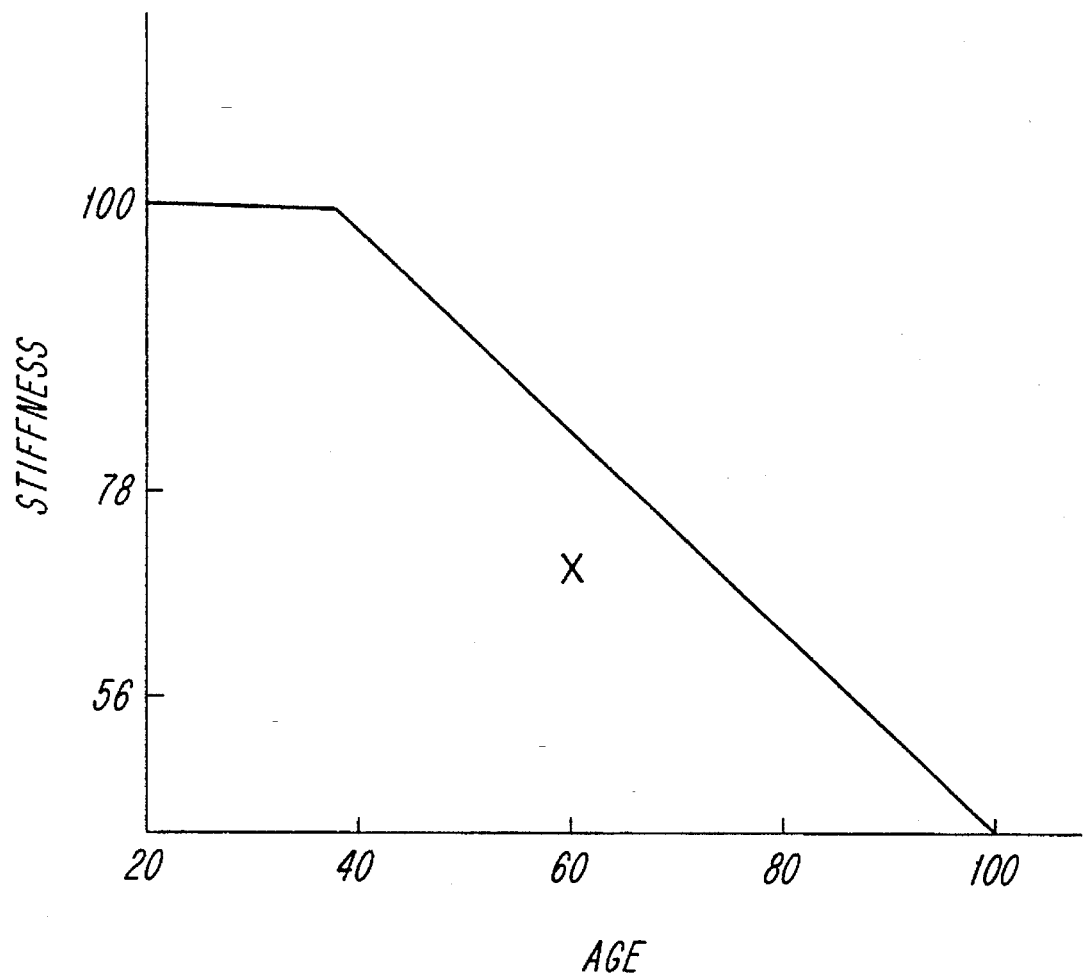
FIG. 17 is an explanator view showing the result of evaluation made by conventional ultrasonic evaluation.

FIGS. 16A–16C show a case of patient who was diagnosed as having osteoporosis, and has undergone medical treatment for a period of one year. FIG. 16A shows a case measured one year ago, 16B a half year ago, and 16C measured recently, respectively.

Compared with the first case which was measured one year ago, the portion where bone structure is increased is sorted by color (the portion painted in black in the figures) so that the effect of medical treatment can readily be recognized (the white portion represents a structure of bone, and marrow is represented by oblique lines in FIGS. 16A and 16C).

A description has been made of an embodiment of the present invention wherein an ultrasonic signal is transmitted to a heel or patella to find a propagation velocity transmitted through a bone, and by a computerized calculation process based on the propagation velocity, an image of a bone in bone structure is displayed. However, not limited to said embodiment, the present invention may also be applied to such an arrangement wherein an image of a bone in bone structure is displayed through computerized calculation process based on information to which both ultrasonic transmission velocity and attenuation ratio of transmitted amplitude are added.

As stated above, a person who has undertaken an examination is able to practically and concretely grasp the progress of osteoporosis by his own eyes by comparing an image of his bone computerized through calculation process and displayed as a geometrical pattern with an image of the bone of a healthy person since the portion where bone structure is reduced is sorted by color.

Further, a person who was diagnosed as having osteoporosis and started a medical treatment can clearly recognize the effect of the treatment since the portion where bone structure is increased with the passage of time is sorted by color.

A cassette to which a container bag is fixed is replaced with a new one every time a new patient is treated so that the risk of infection in hospital by MRSA, Methicillin Resistance *Staphylococcus Aureus,* can be avoided. The patients, most of whom are aged people, can thus take a medical checkup for osteoporosis without any anxiety compared with conventional apparatuses.

While the invention has been particularly shown and described with reference to certain preferred embodiments thereof, it will be understood by those skilled in the art that various changes and modifications may be made without departing from the spirit and scope of the invention.

What is claimed is:

1. A method for evaluating the progress of osteoporosis by utilizing ultrasonic signals comprising the steps of:

transmitting an ultrasonic signal into a heel bone or patella of a person being examined to obtain a propagation velocity of transmission in the bone;

computing a two-dimensional ratio of a compact bone to a bone structure (hereinafter called Au) from a one-dimensional ratio of a compact bone to a bone structure (hereinafter called Eu) based on a propagation velocity obtained according to a calculation formula stated below; and displaying an imitative image of a cross-sectional view of the bone which represents a bone condition of the person being examined based on the obtained Au $$Eu = \frac{\frac{1}{Va} - \frac{1}{Vb}}{\frac{1}{Va} - \frac{1}{Vc}}$$

where,

Vb: Ultrasonic propagation velocity in bone

Va: Ultrasonic propagation velocity in marrow (1500 m/s)

Vc: Ultrasonic propagation velocity in compact bone (3000 m/s), and

Au=Eu×Eu.

2. The method of claim 1 wherein said displaying step comprises drawing an imitative image of a cross-sectional view of the bone by a predetermined computer simulation program using the obtained Au.

3. The method of claim 1 wherein said displaying step comprises selecting the imitative image from among a plurality of images corresponding to different values of Au stored in a computer memory and being identified by an Au, the imitative image being selected as having the same Au as the person being examined.

4. A method for evaluating the progress of osteoporosis by utilizing ultrasonic signals comprising the steps of:

transmitting an ultrasonic signal into a heel bone of a person being examined to obtain a propagation velocity of transmission in the bone;

computing a one-dimensional ratio of a compact bone to a bone structure (hereinafter called Eu) based on a propagation velocity obtained according to a calculation formula stated below;

multiplying the Eu by itself to determine a two-dimensional ratio of a compact bone to a bone structure (hereinafter called Au);

displaying an imitative image of a cross-sectional view of the bone which represents a bone condition of the person being examined based on the obtained Au; and displaying an imitative image of a cross-sectional view of a bone which represents a bone condition of a healthy person in order to compare with the imitative image of the bone of the person being examined $$Eu = \frac{\frac{1}{Va} - \frac{1}{Vb}}{\frac{1}{Va} - \frac{1}{Vc}}$$

where,

Vb: Ultrasonic propagation velocity in bone

Va: Ultrasonic propagation velocity in marrow (1500 m/s), and

Vc: Ultrasonic propagation velocity in compact bone (3000 m/s).

5. The method of claim 4 wherein said step of displaying the bone condition of the person being examined comprises drawing an imitative image of a cross-sectional view of the bone by a predetermined computer simulation program using the obtained Au.

6. The method of claim 4 wherein said step of displaying the bone condition of the person being examined comprises selecting the imitative image from among a plurality of images corresponding to different values of Au stored in a computer memory and being identified by an Au, the imitative image being selected as having the same Au as the person being examined.

7. The method of claim 4 wherein said step of displaying an imitative image of a cross-sectional view of a bone which represents a bone condition of a healthy person comprises choosing from a plurality of images representing various conditions of the bone by age group stored in a computer memory, said choosing step using the age and sex of the person being examined.

8. A method for evaluating the progress of osteoporosis by utilizing ultrasonic signals comprising the steps of:

transmitting an ultrasonic signal into a patella of a person being examined in two directions, a direction substantially horizontal to the patella and a direction intersecting the horizontal direction at a right angle, so as to obtain a propagation velocity of transmission in the bone in both directions;

computing a one-dimensional ratio of a compact bone to a bone structure (hereinafter called Eu) based on the propagation velocity obtained according to a calculation formula stated below;

multiplying the Eu by itself to determine a two-dimensional ratio of a compact bone to a bone structure (hereinafter called Au);

displaying an imitative image of a cross-sectional view of the bone which represents a bone condition of the person being examined based on the obtained Au; and displaying an imitative image of a cross-sectional view of a bone which represents a bone condition of a healthy person in order to compare with the imitative image of the bone of the person being examined $$Eu = \frac{\frac{1}{Va} - \frac{1}{Vb}}{\frac{1}{Va} - \frac{1}{Vc}}$$

where,

Vb: Ultrasonic propagation velocity in bone

Va: Ultrasonic propagation velocity in marrow (1500 m/s), and

Vc: Ultrasonic propagation velocity in compact bone (3000 m/s).

9. The method of claim 8 wherein said step of displaying the bone condition of the person being examined comprises drawing an imitative image of a cross-sectional view of the bone by a predetermined computer simulation program using the obtained Au.

10. The method of claim 8 wherein said step of displaying the bone condition of the person being examined comprises selecting the imitative image from among a plurality of images corresponding to different values of Au stored in a computer memory and being identified by an Au, the imitative image being selected as having the same Au as the person being examined.

11. The method of claim 8 wherein said step of displaying an imitative image of a cross-sectional view of a bone which represents a bone condition of a healthy person comprises choosing from a plurality of images representing various conditions of the bone by age group stored in a computer memory, said choosing step using the age and sex of the person being examined.

12. Apparatus or evaluating the progress of osteoporosis by utilizing ultrasonic signals, comprising:

means for transmitting and receiving ultrasonic signals to and from a heel bone or patella of a person being examined;

means for computing a two-dimensional ratio of a compact bone to a bone structure (hereinafter called Au) based on propagation velocity information of an ultrasonic signal transmitted through the bone structure by said means for transmitting and receiving ultrasonic signals;

means for drawing an imitative image of an inner bone structure according to the obtained Au; and means for displaying the imitative image of the bone which represents a bone condition of the person being examined or of a healthy person.

13. Apparatus for diagnosing osteoporosis, comprising:

a footboard for placing thereon a foot of a person being examined;

a pair of ultrasonic transmitting and receiving transducers provided with probes, said transducers being attached to a base stand on which said footboard is fixed;

moving means for bringing at least either one of said probes in close contact with a foot of a person being examined on the footboard; and an expandable container bag containing water and mixed solution fixed to a cassette, the bag being fixed in a manner to position a protrusion thereof in a lateral direction; and the cassette being fitted to and removed from the probe in a quick operation so as to be replaced for each patient.

* * * * *